United States Patent [19]

Honeybourne et al.

[11] Patent Number: 4,722,905
[45] Date of Patent: Feb. 2, 1988

[54] SEMICONDUCTORS

[75] Inventors: Colin L. Honeybourne, Winterbourne; Richard J. Ewen, Bedminster, both of England

[73] Assignee: National Research Development Corporation, London, England

[21] Appl. No.: 445,711

[22] Filed: Nov. 30, 1982

[30] Foreign Application Priority Data

Dec. 1, 1981 [GB] United Kingdom ............... 8136127

[51] Int. Cl.[4] .......................................... G01N 27/12
[52] U.S. Cl. ....................................... 436/151; 73/23; 338/34; 422/90; 422/98; 436/116
[58] Field of Search ....................... 73/23, 27 R; 260/239 DD; 324/71.5; 338/34; 340/634; 422/98, 90; 436/116, 149, 151

[56] References Cited

U.S. PATENT DOCUMENTS

| 3,930,884 | 1/1976 | Zimmermann et al. | |
|---|---|---|---|
| 3,974,040 | 8/1976 | Siebke et al. | 204/1 T |
| 4,236,307 | 12/1980 | Colla et al. | 324/71.5 |
| 4,381,922 | 5/1983 | Frey et al. | 422/98 |

FOREIGN PATENT DOCUMENTS

| 2334918 | 1/1975 | Fed. Rep. of Germany . |
| 2335403 | 2/1975 | Fed. Rep. of Germany . |
| 1435760 | 5/1976 | United Kingdom . |

OTHER PUBLICATIONS

Kirk-Othmer; Encyclopedia of Chemical Technology, vol. 17, pp. 777-787, 1982.
Wuu et al.; One-dimensional Compounds—II Halogen Oxidation of the Planar Macrocyclic Ni(II) Complex; J. Inorg. Nucl. Chem., vol. 42, pp. 839-842, 1980.
Hiller et al.; 5.14-Dihydro-dibenzo[b.i][5.9.14.18]tetraaza[14]annulen'), ein makrocyclisher Chelat-Bildner Liebigs Ann. Chem. 717, 173-147 (1968).
Müller et al., Makromol. Chem., vol. 179, pp. 2161-2172 (1978), and English translation thereof.
Chemistry and Industry, 19 Apr. 1975, C. L. Honeybourne, "Macrocyclic Dimers of 6-R-benzo-1,4-diazepines".
Inorg. Nucl. Chem. Letters, vol. 10, pp. 715-719, 1974, C. L. Honeybourne et al., "Magnetic Properties of Some Proposed Model Metalloporphins".
Die Makromolekulare Chemie 1976, pp. 2275-2295, R. Mueller et al., "Tetraaza [14] Annulen-Derivate und Thre Vorstuffen, 1".

*Primary Examiner*—Barry S. Richman
*Assistant Examiner*—Michael S. Gzybowski
*Attorney, Agent, or Firm*—Oblon, Fisher, Spivak, McClelland & Maier

[57] ABSTRACT

A gas sensor element comprising a film of a semiconducting compound of formula I supported by a non-conductive substrate, the film being disposed between conductors for supplying a current to the film and withdrawing a current therefrom.

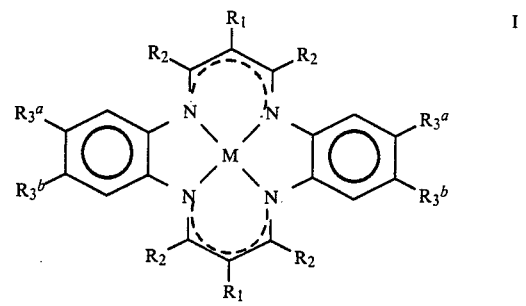

in which:
M represents 2H, Mn, Fe, Co, Ni, Cu, Hg, Cd, Pb, Pt or Pd;
$R_1$ represents H, $CH_3$, Cl, Br, I, CN, $CO_2H$, $COOC_nH_{2n+1}$, $CONH_2$ or $NO_2$;
$R_2$ represents H or $CH_3$; and
$R_3{}^a$ and $R_3{}^b$, which may be identical or different represent H, $NO_2$, Cl, $CO_2H$ or $CH_3$;
provided that when M represents cobalt at least one of $R_1$, $R_2$, $R_3{}^a$ and $R_3{}^b$ is other than hydrogen.

15 Claims, No Drawings

SEMICONDUCTORS

This invention relates to semiconductors useful in thin film gas sensors.

At present, gas sensors which incorporate elements comprising a thin film of the semiconductor copper phthalocyanin, the electrical conductivity of which is increased by sorption of a gas such as NOX, require the elements to be heated to elevated temperatures in order for such sorption to be reversible. Exposure of heated elements to flammable vapours such as $C_5$ hydrocarbons can be hazardous because of the risk of ignition and the life of the sensor element may be limited because of chemical attack thereon by gases such as NOX.

It has now been found that semiconducting thin film gas sensor elements can be produced from certain compounds which enable sensor devices incorporating the elements to be operated at relatively low temperatures, in some cases at ambient.

According to the present invention, a gas sensor element comprises a film of a semiconducting compound of formula I supported by a non-conductive substrate, the film being disposed between conductors for supplying a current to the film and withdrawing a current therefrom.

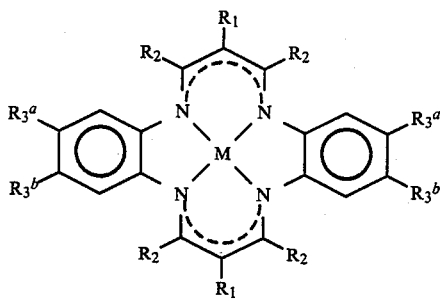

in which:
M represents 2H, Mn, Fe, Co, Ni, Cu, Hg, Cd, Pb, Pt or Pd;
$R_1$ represents H, $CH_3$, Cl, Br, I, CN, $CO_2H$, $COOC_nH_{2n+1}$, $CONH_2$ or $NO_2$;
$R_2$ represents H or $CH_3$ and
$R_3{}^a$ and $R_3{}^b$, which may be identical or different, represent H, $NO_2$, Cl, $CO_2H$ or $CH_3$;
provided that when M represents cobalt at least one of $R_1$, $R_2$, $R_3{}^a$ and $R_3{}^b$ is other than hydrogen.

When the film is required to be highly sensitive to low levels of gas, it is generally preferred that the overall effect of the substituents $R_1$ $R_2$, $R_3{}^a$ and $R_3{}^b$ is electron donating. If $R_1$ is electron withdrawing, e.g. Cl or Br, then at least one of $R^a$ and $R^b$ which are generally identical, usually represents methyl. When, however, the film is required to show satisfactory reversibility of gas uptake at high gas concentrations, the overall effect of the substituents is preferably an electron withdrawing substituent such as Br or $NO_2$.

Generally, compounds in which, when $R_2$ is methyl, $R_1$ is hydrogen are preferred because of ease of accessibility.

When $R_1$ represents $NO_2$, Br, Cl, COOEt, $R_2$ usually represents hydrogen, and at least one of $R^a$ and $R^b$, typically both $R^a$ and $R^b$, usually represents H or methyl.

Compounds in which M represents 2H, Cu or Ni are of particular interest and especially those compounds in which at least one of $R_3{}^a$ and $R_3{}^b$ represents $CH_3$, $R_2$ represents hydrogen, $R_1$ represents $CO_2Et$, $NO_2$, Br, H or $CH_3$ and M represents hydrogen. When M represents Cu it is highly preferred that none of $R_1$, $R_2$, $R_3{}^a$ or $R_3{}^b$ is an electron withdrawing group.

The present invention also includes within its scope, compounds of formula I hereinbefore described per se provided that when M represents Fe and $R_1$ is methyl or chlorine, $R_1$ is other than H or $CH_3$.

Non-metallic compounds of formula I (M=2H) may be produced by reaction of a compound of Formula II

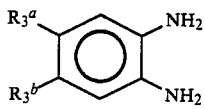

with a compound of formula III $$R_2COCHR_1COR_2 \qquad III$$

typically in a polar solvent such as ethanol, provided that $R_1$ is other than a nitro group. As compounds of formula III in which $R_1$ represents a nitro group, e.g. 2-nitromalondialdehyde, are liable to detonate, it is generally preferable for such compounds II to be treated with an alkali metal salt of III which may exist in the form IV $$A^+O^--C(R_2)C=C(NO_2)COR_2 \qquad IV$$

wherein $A^+$ represents an alkali metal ion.

Once prepared, the macrocycle I may be converted into a metal complex by treatment with a suitable salt of the metal, e.g. an acetate.

Somewhat better yields of metal complexes I are however generally obtained by means of a template reaction in which a complex of II with a metal salt, e.g. an acetate, is reacted with III generally in a polar solvent. In general, sensor elements comprise a non-conductive substrate of e.g. glass or sapphire comprising electrodes in the form of films usually of the order of a micron in thickness, of a conductive metal such as copper, the electrodes being separated by a film of compound I which is also generally about the same thickness as that of the electrodes. A potential difference is applied to the electrodes giving rise to the passage of a current which is generally direct and which is usually very small, e.g. $10^{-12}$ amps. On uptake of gas by the film the conductivity is usually increased dramatically and the change in current is signalled visually or aurally. As the film releases the sorbed gas the conductivity and current passed falls and the system may be so designed that the signal ceases or continues. It is usually unnecessary for the sensor element to be maintained at a temperature greater than 40° C.

Sensors comprising elements according to the present invention are particularly useful for the detection of electron accepting gases and vapours, particularly $NO_2$, $N_2O_4$ and the halogens, for example NOX in diesel fumes produced by machinery in mineshafts. Such sensors are also useful for example in the detection of traces of $NO_2$ in $N_2O$.

The present invention is illustrated by the following Examples:

EXAMPLE 1

Compound A: (I, $R_3{}^a=R_3{}^b=CH_3$; $R_2=H$; $R_1=-CO_2Et$; $M=2H$)

The tetraethyl tetra-acetal of 2-carboxyethylmalondialdehyde ($C_{14}H_{28}O_6$) (59 g) is acidified to pH 5 with aqueous hydrochloric acid (2M). The liberated substituted malondialdehyde is extracted into ether ($5\times100$ ml) and, after removal of the ether in a rotary evaporator, the pale red liquid (29.48 g) is dissolved in dry ethanol (250 ml) and added to 4,5-dimethyl-o-phenylenediamine (27.8 g) in dry ethanol (350 ml). This reaction mixture is stirred continuously in the dark for 60 hours. Filtration yields a bright orange solid, which is then dissolved in chloroform (500 ml). After concentration to 200 ml, slow addition of methanol produces the pure crystalline macrocycle A (5.51 g).

Preparation of Thin Film Sensors

Glass microscope slides, of dimensions $76\times25$ mm, are used as the subtrates upon which the films are prepared. The slides are thoroughly cleaned prior to use. Strips of aluminium foil 5 mm wide are carefully wrapped around the centres of the 76 mm span of the slides to form masks, and copper is deposited in vacuo on to one surface of the slide and foil. The foil strips are then removed, leaving two copper electrodes separated by a 5 mm gap.

The compound under investigation A is applied to the electrodes by vacuum sublimation. A number of electrodes are coated at the same time to ensure a uniform batch of films. The thickness of the films, measured by means of an interference microscope, is in all cases of the order of $10^{-6}$ m.

Sorption and Desorption of Gas

The copper electrodes of the thin film sample, prepared as hereinbefore described, are connected by means of crocodile clips to two electrical feed-throughs (tungsten pins with metal-to-glass seal) of a vacuum chamber. To ensure that a good electrical contact is formed, the electrical resistance between each of the crocodile clips and an additional clip temporarily attached elsewhere on each electrode is measured. When both the contacts have been checked in this way, and found to be satisfactory, the chamber is evacuated to about $10^{-4}$ Pa.

The films are maintained at room temperature and in the dark and a potential of 15 V, obtained from dry batteries, is applied across the film in each case. The current flowing through the film is measured using a Keithley electrometer. The results obtained are given in the form of the changes in the current observed on exposure to various ambients under these conditions.

Prior to the application of NOX to the films, it is established the compound exhibits no response to oxygen-free nitrogen; this gas is then used as a ballast gas into which a measured volume of NOX is injected as the nitrogen is admitted to the previously evacuated vacuum chamber containing the film under investigation. The nitrogen+NOX mixture is admitted to the chamber until the pressure reaches atmospheric pressure. The concentrations of NOX are quoted in parts per million (ppm), and represent estimated upper limits to the actual concentrations present. The actual concentration of NOX quoted at a particular value, however, is constant for all experiments.

In most cases NOX is applied to a film in three concentrations, 10, 100 and 1,000 ppm, each followed by evacuation prior to admission of the next. In all cases the chamber is evacuated to about $10^{-4}$ Pa following each exposure, exposure times varying depending on the response.

Results

When 10 ppm NOX in nitrogen is admitted to the chamber containing the film sensor passing a current of $7\times10^{-12}$ amps, the current rises with progressively decreasing steepness over a period of 15 minutes to an upper limit of about $5\times10^{-11}$. After evacuation for 20 minutes the current returns to $7\times10^{-12}$ amps at which time 100 ppm NOX/nitrogen is admitted and the current rises over a period of about 20 minutes with progressively decreasing steepness to an upper limit $10^{-10}$ amps. Evacuation over about 30 minutes reduces the current to $7\times10^{-12}$ amps at which time 1,000 ppm NOX/nitrogen is admitted and leads to a rise in current over a period of 30 minutes which progressively decreases in steepness and reaches an upper limit at $8\times10^{-10}$ amps.

EXAMPLE 2

Compound B: (I, $R_3{}^a=R_3{}^b=H$; $R_2=H$; $R_1=H$; $M=Cu$)

A given quantity of the required insoluble o-phenylenediamine complex of copper diacetate is suspended in a stirred ethanolic solution of double the molar quantity of malondialdehyde. Although the suspensions change colour very rapidly, vigorous stirring in the dark should continue for 60 hours before filtering off the required product in 40–45% yield.

The complex is highly coloured, very insoluble and does not melt below 300° C. It may be purified by vacuum sublimation at 250° C., although the rate of sublimation is slow.

Sensors are prepared as described in Example 1 and give identical conductivity results when treated with NOX.

EXAMPLE 3

Compound C: (I, $R_3{}^a=R_3{}^b=H$; $R_2=H$; $R_1=CH_3$; $M=Cu$)

Compound C is prepared as described in Example 2 except that malondialdehyde is replaced by 2-methyl-malondialdehyde.

Sensors are prepared as described in Example 1 and give identical conductivity results when treated with NOX.

EXAMPLE 4

Compound D: (I, $R_3{}^a=R_3{}^b=CH_3$; $R_2=H$; $R_1=H$; $M=Cu$)

Compound D is prepared as described in Example 2 except that o-phenylenediamine is replaced by 4,5-dimethyl-o-phenylenediamine.

Sensors are prepared as described in Example 1 and give identical conductivity results when treated with NOX.

EXAMPLE 5

Compound E: (I, $R_3{}^a=R_3{}^b=CH_3$; $R_2=H$; $R_1=Cl$; M=H)

Compound E is produced as described in Example 1 except that the tetraethyl-tetra-acetal of 2-chloromalondialdehyde rather than of 2-carboxyethylmalondialdehyde is used.

Sensors are prepared as described in Example 1 and give the following conductivity result:

Results

When 100 ppm NOX in nitrogen is admitted to the chamber containing the film which passes a current of $5\times10^{-12}$ amps, the current rises with progressively decreasing steepness over about 10 minutes to an upper limit $10^{-11}$ amps. Evacuation over about 10 minutes reduces the current to $5\times10^{-12}$ amps. Introduction of 1,000 ppm NOX in nitrogen then leads to a rise in current over about 20 minutes which progressively decreases in steepness and which reaches an upper limit of about $10^{-9}$ amps. Evacuation over about 20 minutes again reduces the current to $5\times10^{-12}$ amps. The sensors of the present Example are less sensitive than those of Examples 1–4 but release sorbed NOX more readily.

EXAMPLE 6

Compound F: (I, $R_3{}^a=R_3{}^b=CH_3$; $R_2=H$; $R_1=NO_2$; M=2H)

CAUTION: 2-nitromalondialdehyde is a DETONATOR and MUST NOT BE ISOLATED.

The sodium salt of 2-nitromalondialdehyde (13.9 g) is dissolved in ethanol (250 ml) containing 0.1M of glacial acetic acid. To this is added a solution of 4,5-dimethyl o-phenylenediamine (13.6 g) in ethanol (250 ml). The reaction mixture is stirred continously in the dark for 60 hours. The required macrocycle is obtained as a very insoluble bright red solid in 19.8% yield, which analyses satisfactorily without further purification.

Sensors are prepared as described in Example 1 and give conductivity results identical to those of Example 5.

EXAMPLE 7

Compound G: (I, $R_1=R_2=R_3{}^a=R_3{}^b=H$; M=2H)

The compound is prepared as described in Example 1, except that the tetraethyltetracetal of malondialdehyde is used in place of 2-carboxyethylmalondialdehyde and o-phenylenediamine in place of 4,5-dimethyl-o-phenylenediamine. Sensors are prepared as described in Example 1 and give the following conductivity results:

Results

When 10 ppm NOX in nitrogen is admitted to the chamber containing the film sensor which passes a current of about $5\times10^{-12}$ amps, the current rises immediately to about $20^{-11}$ amps. Evacuation reduces the current immediately to $5\times10^{-12}$ amps and admission of 100 ppm NOX in nitrogren leads to an immediate increase in conductivity to about $10^{-10}$ amps. Evacuation again reduces the current to $5\times10^{-12}$ amps and admission of 1,000 ppm NOX/nitrogen raises the current to about $10^{-9}$ amps. Evacuation immediately reduces the current to $5\times10^{-12}$ amps. The film sensors of the present Example are thus both more sensitive and more readily release sorbed NOX than those of the previous Examples.

EXAMPLE 8

Compound H: (I, $R_1=R_2=H$; $R_3{}^a=R_3{}^b=CH_3$; M=2H)

The compound is prepared as described in Example 1 except that malonaldehyde is used in place of 2-carboxyethylmalonaldehyde.

Sensors are prepared as described in Example 1 and give conductivity results identical to those described in Example 7.

What is claimed is:

1. A gas sensor which is highly sensitive to low levels of gas or vapor, which comprises a gas sensitive film of a semiconducting compound, said film being supported on a non-conductive substrate and being disposed between spaced apart conductors, and wherein said semiconducting compound has the formula:

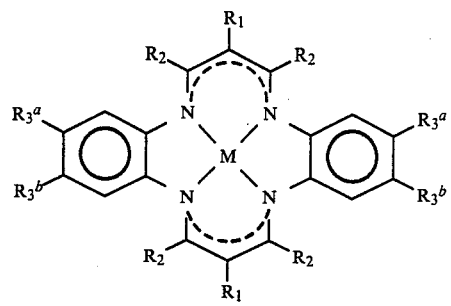

wherein the substituents $R_1$, $R_2$, $R_3{}^a$ and $R_3{}^b$ are electron-donating substituents; or wherein $R_1$ is an electron-withdrawing substituent, $R_2$ is an electron-donating substituent and at least one of $R_3{}^a$ and $R_3{}^b$ is a methyl group and M is selected from the group consisting of 2H, Mn, Fe, Co, Ni, Cu, Hg, Cd, Pb, Pt and Pd.

2. The gas sensor of claim 1, wherein M is 2H, Cu or Ni.

3. The gas sensor of claim 1, wherein the electron-donating substituents $R_1$, $R_2$, $R_3{}^a$ and $R_3{}^b$ are each a methyl group; or at least one of $R_3{}^a$ and $R_3{}^b$ is a methyl group, and the electron-withdrawing substituent $R_1$ is selected from the group consisting of Cl, Br, I, CN, $CO_2H$, $CO_2C_2H_5$, $CONH_2$, $NO_2$ or H.

4. The gas sensor of claim 3, wherein the electron-withdrawing substituent $R_1$ is Cl or Br.

5. A method of detecting low levels of gas or vapor with high sensitivity, which comprises:
   (a) exposing a gas or a vapor to a film of a gas sensor element comprising a gas sensitive film of a semiconducting compound of the formula:

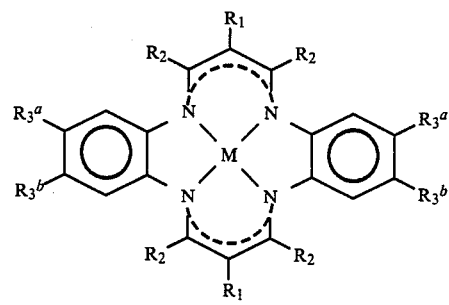

wherein the substituents $R_1$, $R_2$, $R_3{}^a$ and $R_3{}^b$ are electron-donating substituents, or wherein $R_1$ is an electron-withdrawing substituent, $R_2$ is an electron-donating substituent and at least one of $R_3{}^a$ and $R_3{}^b$ is a methyl group and M is selected from the group consisting of 2H, Mn, Fe, Co, Ni, Cu, Hg, Cd, Pb, Pt and Pd; supported on a non-conducting substrate, said film being disposed between spaced apart conductors for supplying a current to the film and withdrawing a current therefrom; while a potential differential is supplied to said film; and (b) applying a current to said film; whereby the current supplied to said film and withdrawn therefrom is increased due to the presence of said gas or vapor, the increase in current being signalled.

6. A gas sensor which is capable of gas uptake at high gas concentrations in which uptake is substantially reversible, which comprises a gas sensitive film of a semiconducting compound, said film being supported on a non-conductive substrate and being disposed between spaced apart conductors, and wherein said semiconducting compound has the formula:

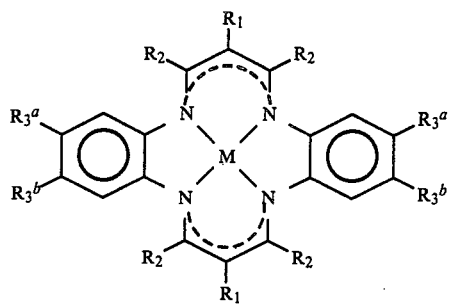

wherein the substituents $R_1$, $R_2$, $R_3{}^a$ and $R_3{}^b$ are electron-withdrawing substituents; and M is selected from the group consisting of 2H, Mn, Fe, Co, Ni, Cu, Hg, Cd, Pb, Pt and Pd.

7. The gas sensor of claim 6, wherein the electron-withdrawing substituents $R_1$, $R_2$, $R_3{}^a$ and $R_3{}^b$ are each selected from the group consisting of Cl, Br, I, CN, $CO_2H$, $CO_2C_2H_5$, $CONH_2$, $NO_2$ or H groups.

8. The gas sensor of claim 7, wherein said $R_1$, $R_2$, $R_3{}^a$ and $R_3{}^b$ groups are each Br or $NO_2$.

9. A method of detecting high concentrations of gas or vapor with a gas sensor whose gas or vapor uptake is substantially reversible, which comprises:

(a) exposing a gas or a vapor to a film of a gas sensor element comprising a gas sensitive film of a semiconducting compound of the formula:

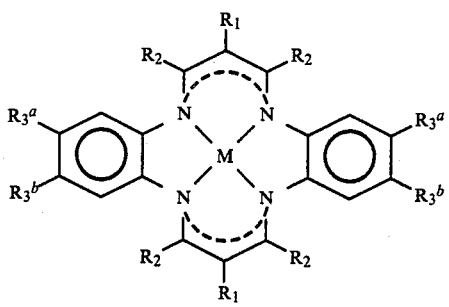

wherein the substituents $R_1$, $R_2$, $R_3{}^a$ and $R_3{}^b$ are electron-withdrawing substituents; and M is selected from the group consisting of 2H, Mn, Fe, Co, Ni, Cu, Hg, Cd, Pb, Pt and Pd; supported on a non-conductive substrate, said film being disposed between spaced apart conductors for supplying a current to the film and withdrawing a current therefrom; while a potential difference is supplied to said film; and (b) applying a current to said film; whereby the current supplied to said film and withdrawn therefrom is increased due to the presence of said gas or vapor, the increase in current being signalled.

10. A gas sensor which is highly sensitive to low levels of gas or vapor, which comprises a gas sensitive film of a semiconducting compound, said film being supported on a non-conductive substrate and being disposed between spaced apart conductors, and wherein said semiconducting compound has the formula:

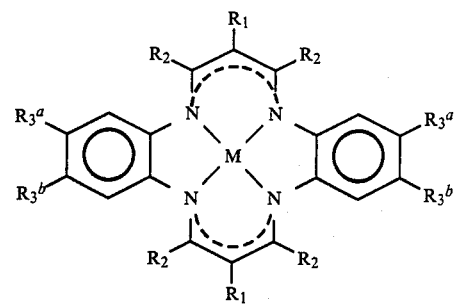

wherein the substituents $R_3{}^a$ and $R_3{}^b$ are each H or $CH_3$, $R_2$ is H, $R_1$ is H, $CH_3$ or $CO_2Et$ and M is selected from the group consisting of 2H, Cu and H.

11. A method of detecting low levels of gas or vapor with high sensitivity, which comprises:

(a) exposing a gas or a vapor to a film of a gas sensor element comprising a gas sensitive film of a semiconducting compound of the formula:

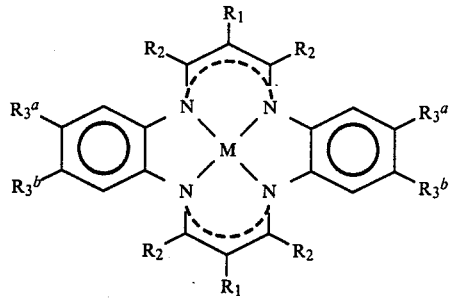

wherein the substituents $R_3{}^a$ and $R_3{}^b$ are each H or $CH_3$, $R_2$ is H, $R_1$ is H, $CH_3$ or $CO_2Et$ and M is selected from the group consisting of 2H, Cu and H; supported on a non-conductive substrate, said film being disposed between spaced apart conductors for supplying a current to the film and withdrawing a current therefrom; while a potential differential is supplied to said film; and (b) applying a current to said film; whereby the current supplied to said film and withdrawn therefrom is increased due to the presence of said gas or vapor, the increase in current being signalled.

12. A gas sensor which is capable of gas uptake at high gas concentrations in which uptake is substantially reversible, which comprises a gas sensitive film of a semiconducting compound, said film being supported on a non-conductive substrate and being disposed between spaced apart conductors, and wherein said semiconducting compound has the formula:

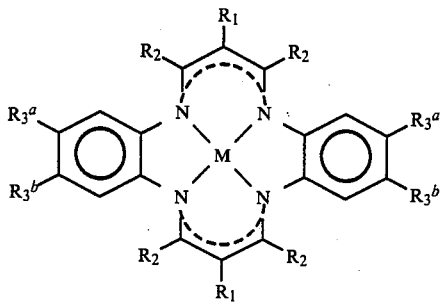

wherein the substituents $R_3{}^a$ and $R_3{}^b$ are each H or $CH_3$, $R_2$ is H, $R_1$ is Cl or $NO_2$; and M is 2H.

13. A method of detecting high concentrations of gas or vapor with a gas sensor whose gas or vapor uptake is substantially reversible, which comprises:

(a) exposing a gas or a vapor to a film of a gas sensor element comprising a gas sensitive film of a semiconducting compound of the formula:

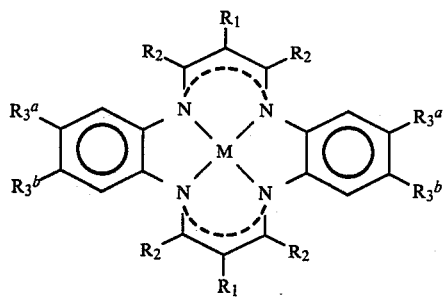

wherein the substituents $R_3{}^a$ and $R_3{}^b$ are each H or $CH_3$, $R_2$ is H, $R_1$ is Cl or $NO_2$; and M is 2H; supported on a non-conductive substrate, said film being disposed between spaced apart conductors for supplying a current to the film and withdrawing a current therefrom; while a potential differential is supplied to said film; and (b) applying a current to the film, whereby the current supplied to said film and withdrawn therefrom is increased due to the presence of said gas or vapor, the increase in current being signalled.

14. A gas sensor which is both highly sensitive to low levels of gas or vapor and also capable of gas uptake at high gas concentrations wherein said uptake uptake is substantially reversible, which comprises a gas sensitive film of a semiconductive compound, said film being supported on a non-conductive substrate and being disposed between spaced apart conductors, and wherein said semiconducting compound has the formula:

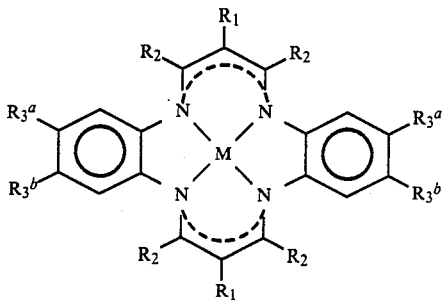

wherein M is 2H and each and all of $R_1$, $R_2$, $R_3{}^a$ $R_3{}^b$ are H.

15. A method of detecting low levels of gas or vapor with high sensitivity or detecting high concentrations of gas or vapor in a substantially reversible manner, which comprises:

(a) exposing a gas or a vapor to a film of a gas sensor element comprising a gas sensitive film of a semiconducting compound of the formula:

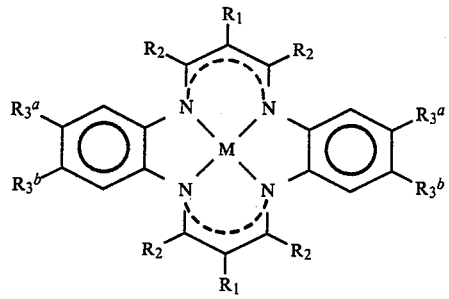

wherein each and all of M, $R_1$, $R_2$, $R_3{}^a$ $R_3{}^b$ are H; supported on a non-conductive substrate, said film being disposed between spaced apart conductors for supplying a current therefrom; while a potential differential is supplied to said film; and (b) applying a current to the film; whereby the current supplied to said film and withdrawn therefrom is increased due to the presence of said gas or vapor, the increase in current being signalled.

* * * * *